US009173589B2

(12) United States Patent (10) Patent No.: US 9,173,589 B2
Chen et al. (45) Date of Patent: Nov. 3, 2015

(54) SYSTEM AND METHOD FOR INERTIAL MAGNETIC RESONANCE ELASTOGRAPHY DRIVER FOR USE WITH INTERVENTIONAL MEDICAL DEVICE

(75) Inventors: Jun Chen, Rochester, MN (US); David A. Woodrum, Kasson, MN (US); Kevin J. Glaser, Rochester, MN (US); Richard L. Ehman, Rochester, MN (US); Phillip J. Rossman, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 314 days.

(21) Appl. No.: 13/435,657

(22) Filed: Mar. 30, 2012

(65) Prior Publication Data

US 2012/0259201 A1 Oct. 11, 2012

Related U.S. Application Data

(60) Provisional application No. 61/469,263, filed on Mar. 30, 2011.

(51) Int. Cl.
*A61B 5/05* (2006.01)
*A61B 5/055* (2006.01)
(Continued)

(52) U.S. Cl.
CPC ............. *A61B 5/055* (2013.01); *A61B 18/22* (2013.01); *G01R 33/285* (2013.01); *G01R 33/56358* (2013.01); *A61B 2018/00577* (2013.01)

(58) Field of Classification Search
CPC .......... G01R 33/56358; G01R 33/285; A61B 5/0048; A61B 5/055; A61B 8/485; A61B 18/22; A61B 2018/00577; F15B 7/00

USPC ......... 324/307, 309, 312, 315, 300, 318, 322; 600/421, 410
See application file for complete search history.

(56) References Cited

U.S. PATENT DOCUMENTS 4,154,228 A 5/1979 Feldstein et al.
5,474,070 A 12/1995 Ophir et al.
(Continued)

FOREIGN PATENT DOCUMENTS

WO 03028800 A2 4/2003

OTHER PUBLICATIONS

Asbach, et al., Assessment of Liver Viscoelasticity Using Multifrequency MR Elastography, Magnetic Resonance in Medicine, 2008, 60:373-379.
(Continued)

*Primary Examiner* — Elmer Chao
(74) *Attorney, Agent, or Firm* — Quarles & Brady, LLP (57) ABSTRACT

A system and method for performing a magnetic resonance elastography (MRE) procedure using an MRI system to monitor operation of a medical device performing a medical procedure. The driver system includes a housing, a port located in the housing and connected to a driving power, and an inertial driver moved within the housing by the driving power. A passage is formed in the housing and extends from a first opening in the housing, through the inertial driver, and to a second opening in the housing. The inertial driver receives a medical device extending through the passage and engages the medical device to impart oscillatory motion thereto as the inertial driver is moved by the driving power. The imparted oscillatory motion travels along the medical device as a waveguide to deliver the oscillatory motion to tissue receiving the medical procedure to perform the MRE procedure.

19 Claims, 8 Drawing Sheets

(51) Int. Cl.
G01R 33/28 (2006.01)
G01R 33/563 (2006.01)
A61B 18/22 (2006.01)
A61B 18/00 (2006.01)

(56) References Cited

U.S. PATENT DOCUMENTS

| | | | |
|---|---|---|---|
| 5,592,085 | A | 1/1997 | Ehman |
| 5,606,971 | A | 3/1997 | Sarvazyan |
| 5,810,731 | A | 9/1998 | Sarvazyan et al. |
| 5,952,828 | A | 9/1999 | Rossman et al. |
| 5,967,991 | A | 10/1999 | Gardineer et al. |
| 5,977,770 | A | 11/1999 | Ehman |
| 6,037,774 | A | 3/2000 | Felmlee et al. |
| 6,486,669 | B1 * | 11/2002 | Sinkus et al. ............... 324/307 |
| 6,862,468 | B2 | 3/2005 | Smith |
| 7,034,534 | B2 | 4/2006 | Ehman et al. |
| 7,307,423 | B2 | 12/2007 | Ehman et al. |
| 7,979,109 | B2 | 7/2011 | Li |
| 2006/0240065 | A1 * | 10/2006 | Chen ............................ 424/423 |
| 2009/0209847 | A1 * | 8/2009 | Li ................................. 600/421 |
| 2009/0295387 | A1 * | 12/2009 | Ehman et al. ................ 324/309 |

OTHER PUBLICATIONS

Bensamoun, et al., Determination of Thigh Muscle Stiffness Using Magnetic Resonance Elastography, Journal of Magnetic Resonance Imaging, 2006, 23:242-247.

Bensamoun, et al., Measurement of Liver Stiffness With Two Imaging Techniques: Magnetic Resonance Elastography and Ultrasound Elastometry, Journal of Magnetic Resonance Imaging, 2008, 28:1287-1292.

Chan, et al., Shear Waves Induced by Moving Needle in MR Elastography, Proceedings of the 26th Annual International Conference of the IEEE EMBS, San Francisco, CA, Sep. 1-5, 2004, pp. 1022-1024.

Chan, et al., Needle Shear Wave Driver for Magnetic Resonance Elastography, Magnetic Resonance in Medicine, 2006, 55:1175-1179.

Chen, et al., Early Detection of Nonalcoholic Steatohepatitis in Patients with Nonalcoholic Fatty Liver Disease by Using MR Elastography, Radiology, 2011, 259(3):749-756.

DeWall, et al., Shear Wave Velocity Imaging Using Transient Electrode Perturbation: Phantom and Ex Vivo Validation, IEEE Transactions on Medical Imaging, 2011, 30(3):666-678.

Garcia-Medina, et al., In Vivo Evaluation of a MR-Guided 980nm Laser Interstitial Thermal Therapy System for Ablations in Porcine Liver, Lasers in Surgery and Medicine, 2011, 43:298-305.

Goldberg, et al., Thermal Ablation Therapy for Focal Malignancy: A Unified Approach to Underlying Principles, Techniques, and Diagnostic Imaging Guidance, AJR, 2000, 174:323-331.

Goldberg, et al., Image-Guided Tumor Ablation: Proposal for Standardization of Terms and Reporting Criteria, Radiology, 2003, 228:335-345.

Huwart, et al., Liver Fibrosis: Noninvasive Assessment with MR Elastography Versus Aspartate Aminotransferase-to-Platelet Ratio Index, Radiology, 2007, 245(2):458-466.

Huwart, et al., Magnetic Resonance Elastography for the Noninvasive Staging of Liver Fibrosis, Gastroenterology, 2008, 135(1):32-40.

Jansen, et al., Outcome of Regional and Local Ablative Therapies for Hepatocellular Carcinoma: A Collective Review, EJSO, 2005, 31:331-347.

Kei, et al., Local Tumor Progression After Radiofrequency Ablation of Liver Tumors: Analysis of Morphologic Pattern and Site of Recurrence, AJR, 2008, 190:1544-1551.

Kruse, et al., Magnetic Resonance Elastography of the Brain, Neuroimage, 2008, 39(1):231-237.

Le, et al., Feasibility of Simultaneous Temperature and Tissue Stiffness Detection by MRE, Magnetic Resonance in Medicine, 2006, 55:700-705.

Lee, et al., MR Elastography in Renal Transplant Patients: A Feasibility Study, Proc. Intl. Soc. Mag. Reson. Med., 2011, 19:2949.

Manduca, et al., Magnetic Resonance Elastography: Non-Invasive Mapping of Tissue Elasticity, Medial Image Analysis, 2001, 5:237-254.

McKnight, et al., MR Elastography of Breast Cancer: Preliminary Results, AJR, 2002, 178:1411-1417.

Murphy, et al., Analysis of Time Reduction Methods for Magnetic Resonance Elastography of the Brain, Magnetic Resonance Imaging, 2010, 28:1514-1524.

Muthupillai, et al., Magnetic Resonance Elastography by Direct Visualization of Propagating Acoustic Strain Waves, Science, 1995, 269:1854-1857.

Rieke, et al., MR Thermometry, Journal of Magnetic Resonance Imaging, 2008, 27:376-390.

Ringleb, et al., Applications of Magnetic Resonance Elastography to Healthy and Pathologic Skeletal Muscle, Journal of Magnetic Resonance Imaging, 2007, 25:301-309.

Rossman, et al., Piezoelectric Bending Elements for Use as Motion Actuators in MR Elastography, Proc. Intl. Soc. Mag. Reson. Med., 2003, 11:1075.

Sapareto, et al., Thermal Dose Determination in Cancer Therapy, Int. J. Radiation Oncology Biol. Phys., 1984, 10 (6):787-800.

Sapin-de Brosses, et al., Temperature Dependence of the Shear Modulus of Soft Tissues Assessed by Ultrasound, Physics in Medicine and Biology, 2010, 55:1701-1718.

Stafford, et al., Elastographic Imaging of Thermal Lesions in Soft Tissue: A Preliminary Study In Vitro, Ultrasound in Med. & Biol., 1998, 24(9):1449-1458.

Talwalkar, Elastography for Detecting Hepatic Fibrosis: Options and Considerations, Gastroenterology, 2008, 135 (1):299-302.

Talwalkar, et al., Magnetic Resonance Imaging of Hepatic Fibrosis: Emerging Clinical Applications, Hepatology, 2008, 47:332-342.

Talwalkar, et al., Feasibility of In Vivo MR Elastographic Splenic Stiffness Measurements in the Assessment of Portal Hypertension, AJR, 2009, 193:122-127.

Wang, et al., Assessment of Chronic Hepatitis and Fibrosis: Comparison of MR Elastography and Diffusion-Weighted Imaging, AJR, 2011, 196:553-561.

Wu, et al., Assessment of Thermal Tissue Ablation With MR Elastography, Magnetic Resonance in Medicine, 2001, 45:80-87.

Yin, et al., A Preliminary Assessment of Hepatic Fibrosis with Magnetic Resonance Elastography, Clin. Gastroenterol. Hepatol., 2007, 5(10):1207-1213.

* cited by examiner

SYSTEM AND METHOD FOR INERTIAL MAGNETIC RESONANCE ELASTOGRAPHY DRIVER FOR USE WITH INTERVENTIONAL MEDICAL DEVICE

CROSS-REFERENCE TO RELATED APPLICATION

This application claims the benefit of U.S. Provisional Patent Application No. 61/469,263 filed Mar. 30, 2011, the disclosure of which is hereby incorporated by reference in its entirety.

STATEMENT REGARDING FEDERALLY SPONSORED RESEARCH

This invention was made with government support under EB001981 awarded by the National Institutes of Health. The government has certain rights in this invention.

BACKGROUND OF THE INVENTION

The field of the invention is nuclear magnetic resonance imaging methods and systems. More particularly, the invention relates to devices for implementing magnetic resonance elastography (MRE) in conjunction with the use of insertable or interventional medical devices.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging (MRI) systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient, a physician can feel differences in the compliance of tissues and detect the presence of tumors and other tissue abnormalities. Unfortunately, this valuable diagnostic tool is limited to those tissues and organs that the physician can feel, and many diseased internal organs go undiagnosed unless the disease happens to be detectable by one of the above imaging modalities. Tumors that are undetected by existing imaging modalities and cannot be reached for palpation through the patient's skin and musculature, are often detected by surgeons by direct palpation of the exposed organs at the time of surgery. Palpation is a common method for detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the MR signals, and from this the mechanical properties of the subject can be determined. In many applications, the production of shear waves in the tissues is merely a matter of physically vibrating the surface of the subject with an electromechanical device such as that disclosed in U.S. Pat. No. 5,592,085. For example, shear waves may be produced in the breast by placing the breast in direct contact with the oscillatory device. Also, with organs like the liver that are difficult to directly palpate, shear waves can be produced indirectly within the tissue by applying the oscillatory force to the exterior surface of the body and allowing the waves to propagate into the organ.

A number of driver devices have been developed to produce the oscillatory force needed to practice MRE. As disclosed in U.S. Pat. Nos. 5,977,770, 5,952,828, 6,037,774, and 6,486,669, these typically include a coil of wire through which an alternating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver system as described in U.S. Pat. Nos. 7,034,534 and 7,307,423. The acoustic driver system includes an active driver located remotely from the MRI system and acoustically coupled by a tube to one or more passive drivers positioned on the subject being imaged. The passive drivers do not disturb the magnetic fields and may be oriented in any direction.

MRE-based tissue stiffness measurements could be important for detecting prostate and rectal cancer, and evaluating the cancer cell death due to thermal ablation. However, these tissues of interest are deep in the body surrounded by normal soft tissues, which makes the conventional external MRE driver not optimal because the waves are not significantly attenuated as they propagate toward these deeper tissues.

On the other hand, some existing MRI-related applications that use insertable catheters, such as endourethral/endorectal MRI and MRI-guided percutaneous thermal ablation, have the benefit of direct access to the tissue in the vicinity of the tip of the catheter where RF coils and heat sources are located, which results in better imaging SNR and better ablation reliability respectively. To measure the MRE-based tissue stiffness in the vicinity of catheter, the above-described conventional external MRE drivers are not suitable because the driver needs to be physically positioned on the surface of the subject's body, and often must be fastened by a supporting belt or frame, which increases the potential for positioning conflicts with the catheter. Furthermore, the above-described conventional, external MRE drivers are not suitable because the wave SNR is degraded because of tissue attenuation along the distance between the external driver and the tissue of interest at the tip of the catheter.

Therefore, it would be desirable to have a system and method for performing MRE studies of organs, such as the prostate, and other areas of the body that are not amenable to MRE imaging using traditional MRE drivers due to particular internal locations in the body, such as near other tissue structures that impede the delivery of the requisite waves to the target tissue. Additionally, it would be desirable to have a system and method for performing MRE studies during insertable or interventional procedures without impeding the clinician's ability to seek positions desirable for the interventional procedure and without degraded wave SNR caused by the insertable or interventional device.

SUMMARY OF THE INVENTION

The present invention overcomes the aforementioned drawback by providing an inertial MRE driver that is configured to be coupled to an insertable or interventional device.

The inertial MRE driver is driven through a pneumatic connection to receive pressure waves thereby overcoming the need to locate active drive elements within a bore of an MRI system or that otherwise interfere with the use of the insertable or interventional device. Specifically, a housing is provided that is connected to the pneumatic connection and substantially surrounds a portion of an insertable or interventional medical device that is designed to be located remotely from a portion of the insertable or interventional medical device to be directed to the target tissue. A piston is located within the housing and is driven through the pneumatic connection to impart oscillatory energy to the insertable or interventional device to direct the oscillatory energy toward the target tissue. In this regard, the insertable or interventional device is used by the inertial MRE drive as a waveguide to direct the oscillatory energy, which is highly controlled to perform an MRE study, toward the target tissue.

Accordingly, an inertial MRE driver is provided that can be coupled with a new or an existing medical system designed for insertion or interventional procedures without any hardware and software modification to the medical system. The possible positioning interference between a traditional, external MRE driver and the medical system is avoided because the inertial MRE driver does not attach to the patient and it does not contact with the subject's body. The wave SNR produced by the inertial MRE driver is improved at the target tissue because the medical device system is used to transmit mechanical waves directly from the inertial MRE driver to the target tissue.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present invention is employed in a system such as that described in the previously-cited U.S. Pat. No. 5,592,085 which provides a system and method for measuring the strain in gyromagnetic materials, such as tissues, using MR methods and apparatus and is incorporated herein by reference. The present invention may also be employed with other medical imaging modalities including, but not limited to, ultrasound.

Figure 1:
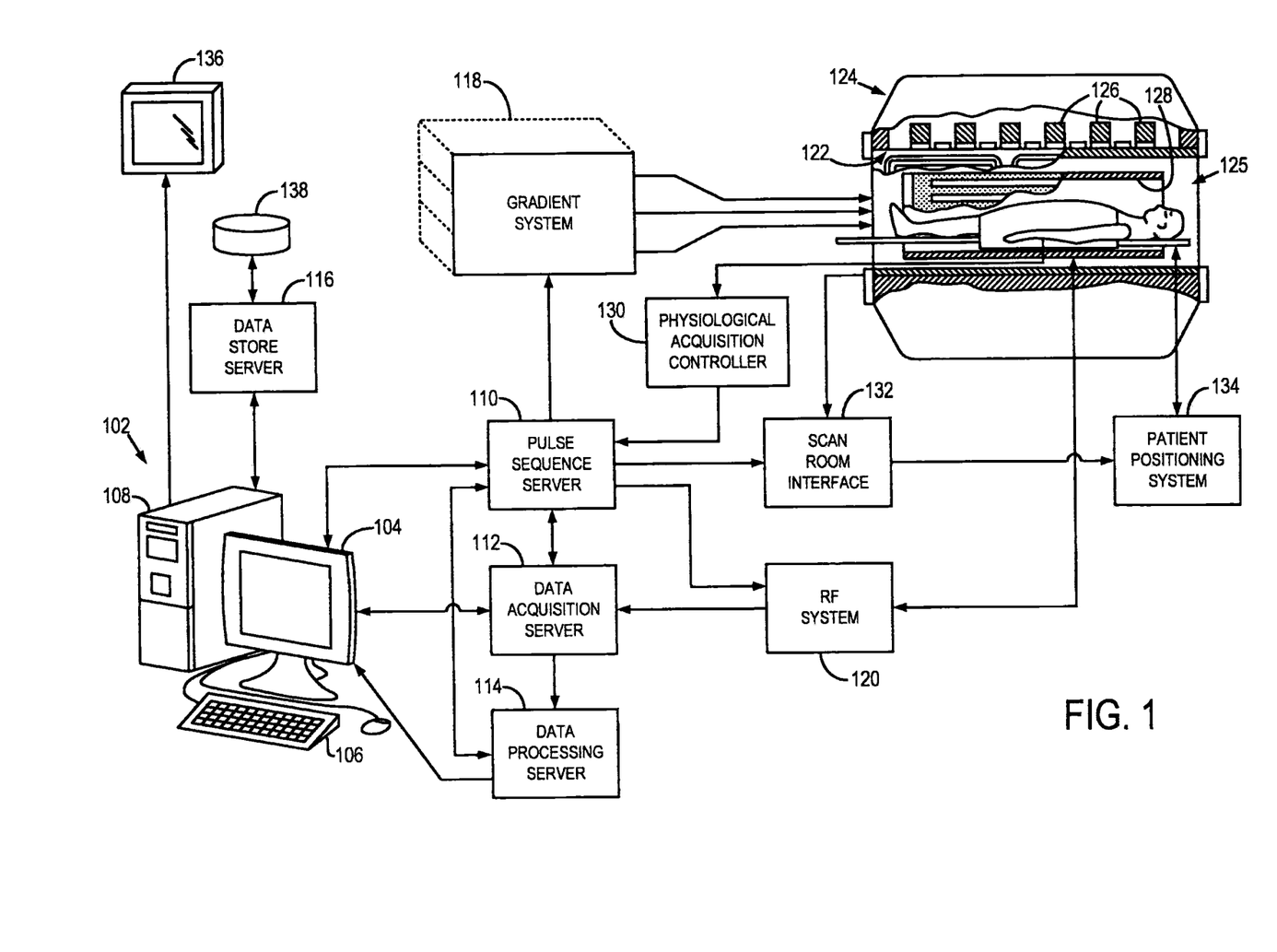
FIG. 1 is a block diagram of a magnetic resonance imaging ("MRI") system that employs the present invention.

Referring to FIG. 1, the preferred embodiment of the invention is employed in a magnetic resonance imaging ("MRI") system 100. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 extending about a bore 125 formed there through and includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad \text{Eqn. (1);}$$

and the phase of the received MR signal may also be determined:

$$\phi = \tan^{-1}\left(\frac{Q}{I}\right). \qquad \text{Eqn. (2)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
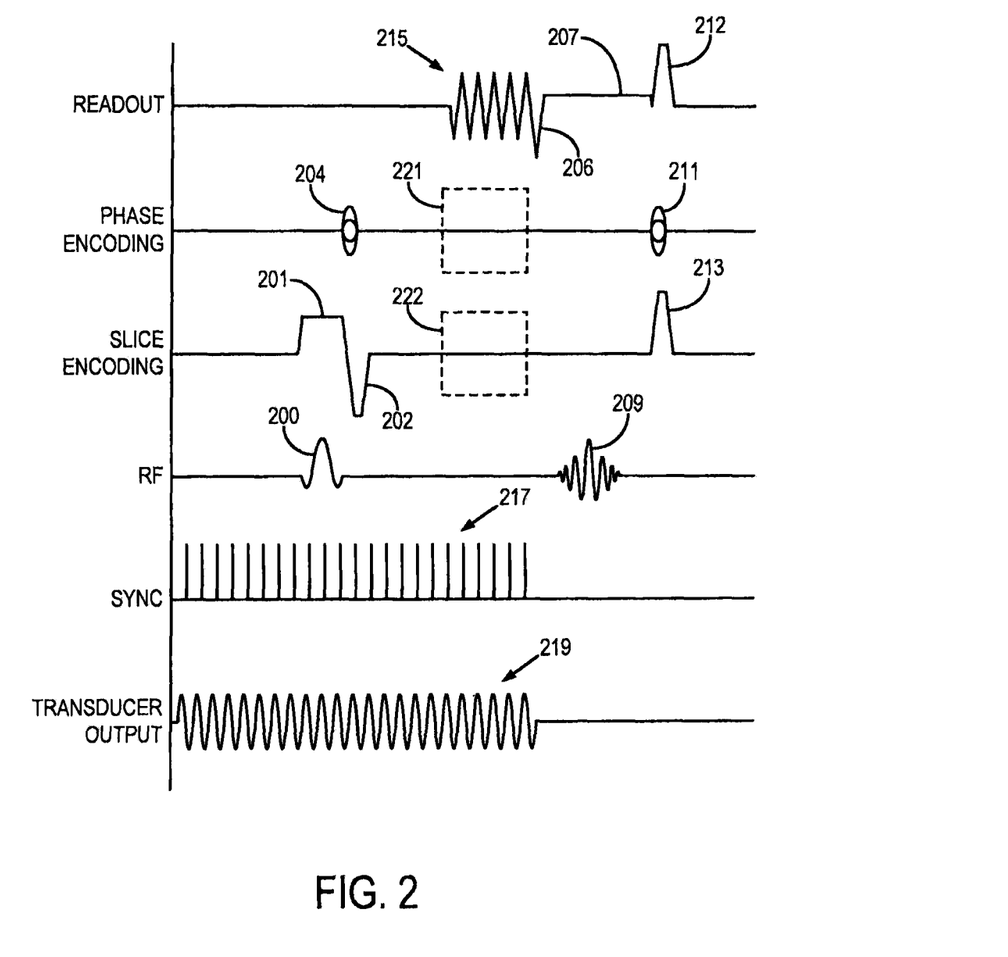
FIG. 2 is a graphic representation of an exemplary magnetic resonance elastography ("MRE") pulse sequence employed by the MRI system of FIG. 1.

Referring particularly to FIG. 2, an exemplary pulse sequence, which may be used to acquire magnetic resonance ("MR") data according to an embodiment of the present invention, is shown. The pulse sequence is fundamentally a 2DFT pulse sequence using a gradient recalled echo. Transverse magnetization is produced by a selective 90 degree radiofrequency ("RF") excitation pulse 200 that is produced in the presence of a slice select gradient, $G_z$, pulse 201 and followed by a rephasing gradient pulse 202. A phase encoding gradient, $G_y$, pulse 204 is then applied at an amplitude and polarity determined by the view number of the acquisition. A read gradient, $G_x$, waveform is applied as a negative dephasing lobe 206, followed by a positive readout gradient pulse 207. An MR echo signal 209 is acquired 40 milliseconds after the RF excitation pulse 200 during the readout pulse 207 to frequency encode the 256 digitized samples. The pulse sequence is concluded with spoiler gradient pulses 212 and 213 along read and slice select axes, and a rephasing gradient pulse 211 is applied along the phase encoding axis ("$G_y$-axis"). As is well known in the art, this rephasing pulse 211 has the same size and shape, but opposite polarity of the phase encoding pulse 204. The pulse sequence is repeated 128 times with the phase encoding pulse 204 stepped through its successive values to acquire a 128-by-256 array of complex MR signal samples that comprise the data set.

An alternating magnetic field gradient is applied after the transverse magnetization is produced and before the MR signal is acquired. In the pulse sequence illustrated in FIG. 2, the read gradient, $G_x$, is used for this function and is alternated in polarity to produce bipolar, gradient waveforms 215. The frequency of the alternating gradient 215 is set to the same frequency used to drive the MRE transducer, and it typically has a duration of 25 milliseconds. At the same time, the pulse sequence server 110 produces synchronizing ("sync") pulses 217, which have the same frequency as and have a specific phase relationship with respect to the alternating gradient pulses 215. These sync pulses 217 are used to produce the drive signals for the magnetic resonance elastography ("MRE") transducer to apply an oscillating stress 219 to the patient. To insure that the resulting waves have time to propagate throughout the field of view, the sync pulses 217 may be turned on well before the pulse sequence begins, as shown in FIG. 2.

The phase of the MR signal 209 is indicative of the movement of the spins. If the spins are stationary, the phase of the MR signal is not altered by the alternating gradient pulses 215, whereas spins moving along the read gradient axis ("$G_x$-axis") will accumulate a phase proportional to their velocity. Spins which move in synchronism and in phase with the alternating magnetic field gradient 215 will accumulate maximum phase of one polarity, and those which move in synchronism, but 180 degrees out of phase with the alternating magnetic field gradient 215 will accumulate maximum phase of the opposite polarity. The phase of the acquired MR signal 209 is thus affected by the "synchronous" movement of spins along the $G_x$-axis.

The pulse sequence in FIG. 2 can be modified to measure synchronous spin movement along the other gradient axes ($G_y$ and $G_z$). For example, the alternating magnetic field gradient pulses may be applied along the phase encoding axis ("$G_y$-axis") as indicated by dashed lines 221, or they may be applied along the slice select axis ("$G_z$-axis") as indicated by dashed lines 222. Indeed, they may be applied simultaneously to two or three of the gradient field directions to "read" synchronous spin movements along any desired direction.

MRE may be implemented using most types of MR imaging pulse sequences. Gradient echo sequences can be readily modified to incorporate the alternating gradient as illustrated in the above-described embodiment. In some cases, however, the characteristics of a gradient echo sequence may not be ideal for a particular application of the technique. For example, some tissues (such as those with many interfaces between materials with dissimilar magnetic susceptibilities) may have a relatively short $T^*_2$ relaxation time and, therefore, may not provide enough signal to obtain a noise-free image at the required echo delay time. In this setting, a spin echo implementation of the invention may be ideal, because for a given echo delay time ("TE"), this pulse sequence is much less sensitive to susceptibility effects than a gradient echo sequence. When a spin echo pulse sequence is used, the alternating magnetic field gradient can be applied either before and/or after the 180 degree RF inversion pulse. However, if the alternating gradient is applied both before and after the RF inversion pulse, the phase of the alternating magnetic field gradient must be inverted 180 degrees after the RF inversion pulse in order to properly accumulate phase.

The physical properties of tissue are measured using MRE by applying a stress and observing the resulting strain. For example a tension, pressure, or shear is applied to a subject and the resulting elongation, compression, or rotation is observed. By measuring the resulting strain, elastic properties of the tissue such as Young's modulus, Poisson's ratio, shear modulus, and bulk modulus can be calculated. Moreover, by applying the stress in all three dimensions and measuring the resulting strain, the elastic properties of the tissue can be completely defined.

The attenuation of the strain wave can be estimated by observing the rate at which the strain decreases as a function of distance from the stress producing source. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Figure 3:
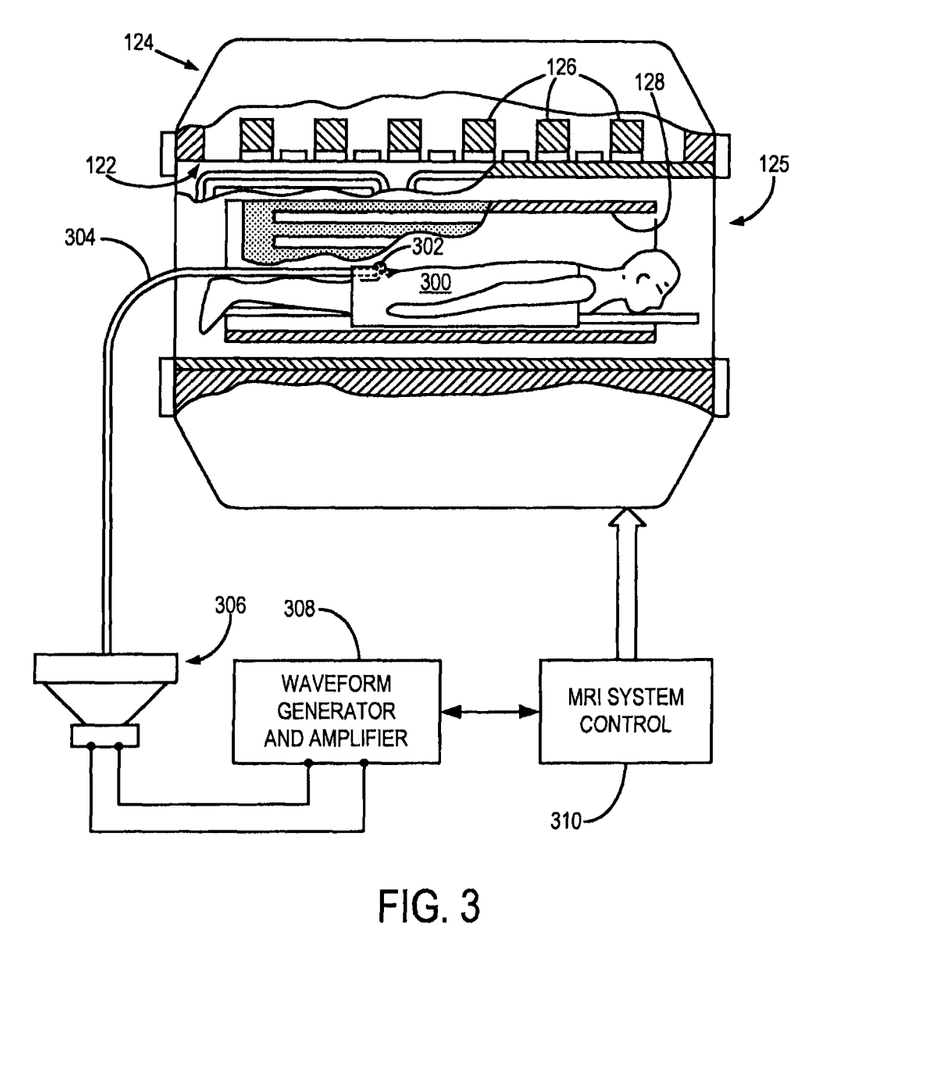
FIG. 3 is a block diagram of a portion of the MRI system of FIG. 1 showing an MRE driver system and associated medical device, wave generator, and amplifier assembly, in accordance with the present invention.

Referring to FIG. 3, the present invention is an MRE driver system designed to be coupled to a medical device that may be inserted or otherwise interventionally positioned within the subject 300 and energized to produce an oscillating stress. It includes a pressure-activated, inertial driver 302, which, as will be described in detail, is coupled to a medical device designed to be inserted or interventionally positioned proximate to a region of interest in the subject 300 to use the medical device as a waveguide to enable MRE imaging of the region of interest coordinated with the medical procedure performed with the medical device. The driver 302 is connected to an inlet tube 304 to a remotely located driver power assembly 306. The driver power assembly 306 may be pneumatic, for example, and is remote from the bore 125 of the magnet assembly 124 in the sense that it is away from the strong magnet fields produced by the magnet assembly 124 where its operation is not impeded by those fields, and where its operation will not perturb the MRI system magnetic fields. The driver power assembly 306 is electrically driven by a waveform generator and amplifier 308, which in turn is controlled by the pulse sequence server 110 in the MRI system control 310. The MRI system control 310 directs the MRI system to perform an MRE scan by driving the RF coil 128, and the gradient coils 122 in the magnet assembly 124 to perform a series of pulse sequences, such as described above, while enabling the waveform generator 308 at the proper moment during each pulse sequence to apply an oscillatory stress to the subject 300.

Figure 4:
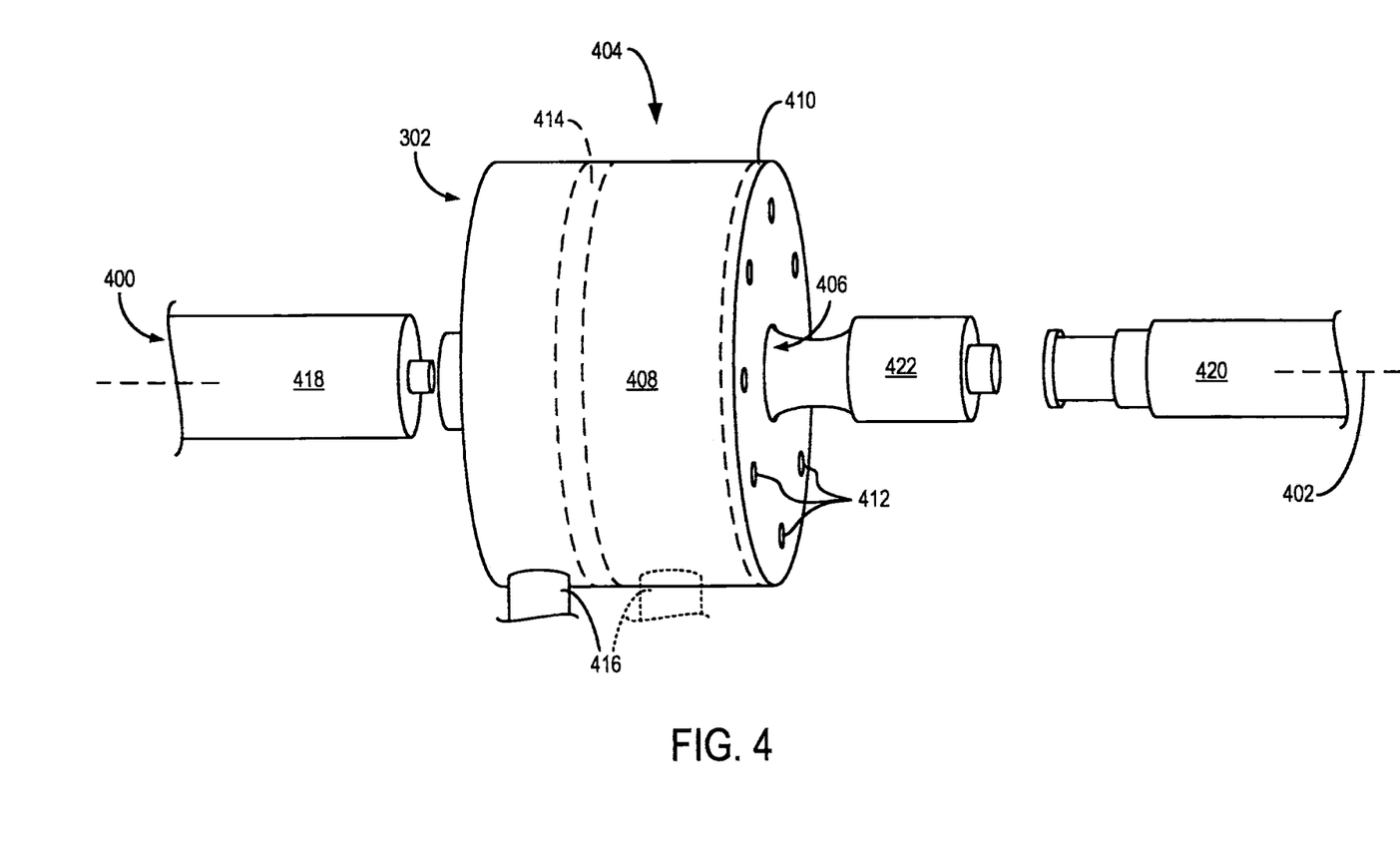
FIG. 4 is a perspective view of a configuration of the MRE driver and medical device of FIG. 3 in accordance with the present invention.

Referring now to FIG. 4, a configuration of the inertial MRE driver 302 and associated medical device 400 is illustrated in further detail. As described above, the medical device 400 is an insertable or otherwise interventional medical device, for example, such as a laser ablation applicator or the like. As illustrated, the medical device 400 is coupled with the MRE driver 302 and, in the illustrated configuration, extends through the MRE driver 302 along a longitudinal axis 402 of the medical device 400. Specifically, the MRE driver 302 includes a housing 404 that includes a passage 406 formed therein to allow the medical device 400 to extend through the passage 406. Specifically, the housing 404 includes an enclosure wall 408 and, connected thereto, a cover 410. The cover 410 may include a plurality of openings 412 that, as will be described, are designed to allow air from within an internal housing chamber defined by the enclosure wall 408 and the cover 410 to be displaced through the openings 412, such that the cover 410 operates as a pressure balancing cover.

As will be described in detail with respect to FIG. 5, an inertial driver, such as a piston 414 (shown in phantom), is arranged within the housing 404 and is configured to be actuated by a driving power received through a port 416 formed in the housing 414 that is configured to connect the MRE driver 302 to the inlet tube 304 to receive the driving power from the remotely located driver power assembly 306, of FIG. 3. As illustrated, the port 416 may be arranged to be positioned on either side or, in some situations, may be arranged on both sides of the piston 414. In the case of being arranged on both sides of the piston 414, the pair of ports 416 are coupled to respective driving energies that are out of phase so as to coordinate driving the piston 414 in a reciprocal fashion.

The piston 414, as will be described, may be engaged with the medical device 400. Accordingly, it is contemplated that, although not required, the medical device 400 may be configured to be disassembled, such that a proximal portion 418 and a distal portion 420 can be disconnected from a central portion 422 that extends through the housing 404 and, as will be described, may connect to the piston 414.

Figure 5:
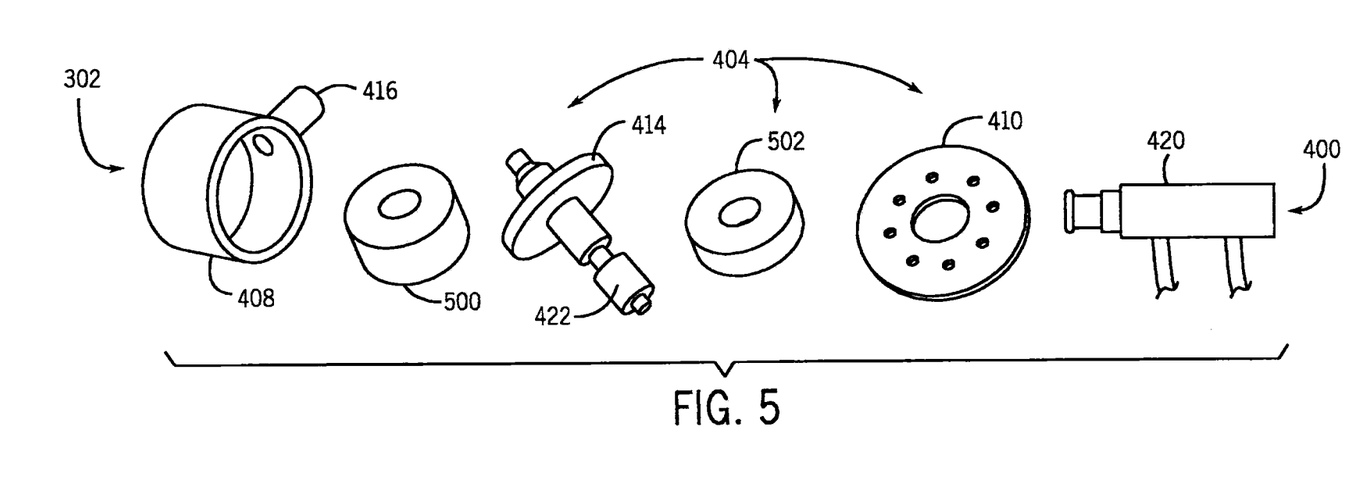
FIG. 5 is an exploded view of the MRE driver and medical device of FIGS. 3 and 4.

Referring now to FIG. 5, The MRE driver 302 and medical device 400 are shown in exploded form. Primarily, FIG. 5 shows the internal components of the MRE driver 302 located within the housing 404 and the central portion 422 of the medical device 400. Specifically, as described above, the piston 414 surrounds and may be affixed to the central portion 422 of the medical device 400 such that motion of the piston 414 along the longitudinal axis 402 of FIG. 4 causes similar motion of the central portion 422 of the medical device 400. To counterbalance motion of the piston 414, a pair of biasing members 500, 502, illustrated as fiber springs, are arranged within the housing 404 on opposing sides of the piston 414. Accordingly, when the piston 414 and central portion 422 of the medical device 400 is driven in one direction, one of the biasing members 500, 502 resists that motion and biases the piston 414 and central portion 422 of the medical device 400 away from an extreme position. Accordingly, reciprocal motion by the piston 414 translated into inertial oscillatory motion of the medical device 400.

Figure 6:
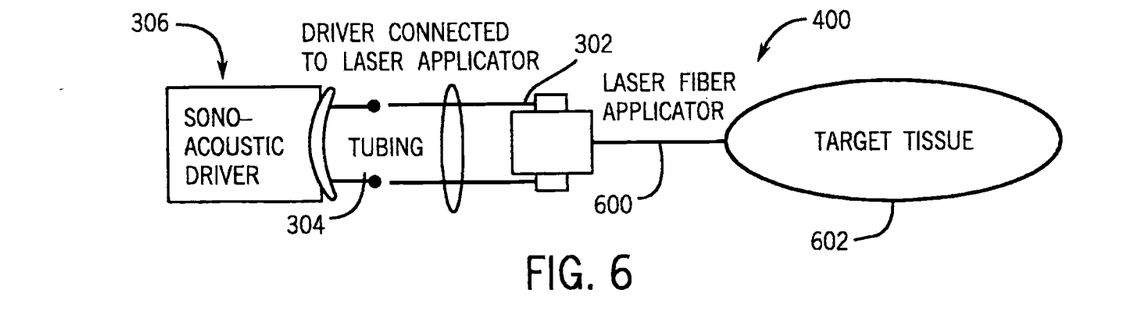
FIG. 6 is a schematic view of the MRE driver and medical device during a medical procedure.

Referring to FIG. 6, this configuration results in the medical device 400, which in the configuration illustrated in FIG. 6 is a laser applicator, acting as a waveguide to translate the above-described inertial oscillatory motion along an extent 600 of the medical device 400 to a target tissue 602 located within a subject. As illustrated in FIGS. 3-6, the medical device 400 extends through the inertial driver 302 without modification, for example, in the illustrated configuration, without modification of the original hardware of the laser ablation system. However, in one configuration, it is contemplated that the connections between the proximal portion 418, central portion 422, and distal portion 420 of the medical device 400 may be achieved using IV connectors. In this case, because the inertial driver 302 is inserted between the original laser source and applicator by the standard IV connectors, the IV connection is sealed so that the saline circulation for cooling the tip of applicator will not be disturbed.

As mentioned previously, percutaneous tumor ablation has become an important nonsurgical treatment for primary and secondary malignant hepatic tumors. A critical part of the tumor ablation is intra-treatment monitoring to determine whether an adequate treatment is achieved. A recent study looking at long-term efficacy of radiofrequency ablation in treatment of liver tumors over a 6 year period demonstrated that there was a high concordance rate (87%) between the exact sites of local tumor progression and insufficient ablative margin. However, measuring tissue temperature change with MRI remains difficult because it depends on calculated damage and cell death assumptions from the Arrehenius equation. Temperature change is only for a short time, and it is difficult to be sure that the tissue is reliably ablated. It would be preferable to monitor the treatment with a method that can potentially image cellular death. Thermal ablation has been linked to increased stiffness in tissue due to thermally induced random reorganization of denatured proteins. The present invention enables the imaging of changes in tissue stiffness, which thereby provides an image of the actual cellular death and protein denaturation.

Testing of the above-described driver 302 providing a path-thru configuration was performed first in phantom studies then in porcine liver. Phantom studies used agarose gel phantom. The laser applicator was constructed from optically transparent, flexible, polycarbonate tubing with a diameter of 1.65 mm (17 Ga, 5 F) with a usable length of 11 inches. Introduction is accomplished by using a titanium trochar and 14 Ga Teflon catheter as a guide. After placement of the catheter, the trochar was removed and replaced with the laser applicator. The Teflon catheter was then pulled back over the shaft of the applicator prior to laser delivery. For the in vivo studies, the laser applicator was placed in the liver using intermittent MR guidance. During the ablation, MR elastography was performed at 40 second intervals to monitor the changing stiffness. Ablations were performed for 2 minutes.

The path-thru driver was made to vibrate the laser applicator to act as a waveguide as described above. The diameter of the driver was 4 cm, and height was 2.5 cm; it connected to the standard laser applicator and the laser source equipment. The laser fiber tip went through the driver and allowed saline circulation through the laser applicator.

An SE-EPI based MRE sequence was developed and performed on a 1.5 T scanner, using an FOV=26 cm, phase offsets=3, and MENC=24 µm/pi-radian. The imaging plane was orthogonal to the laser applicator, the number of slices=15, the slice position covered the laser ablation lesion, and the motion sensitizing direction included all three orthogonal directions. A matrix of 72×72, a fractional phase FOV=1, NEX=1, Bandwidth=250 kHz, TE/TR=1250/55 msec, slice thickness=5 mm, scan time=30 sec, mechanical frequency=120 Hz were used. The MRE inversions were 3D phase gradient inversions, with 3D directional filters (cutoff frequency 0.1-80 wave/FOV) for calculating MR elastograms.

Figure 7:
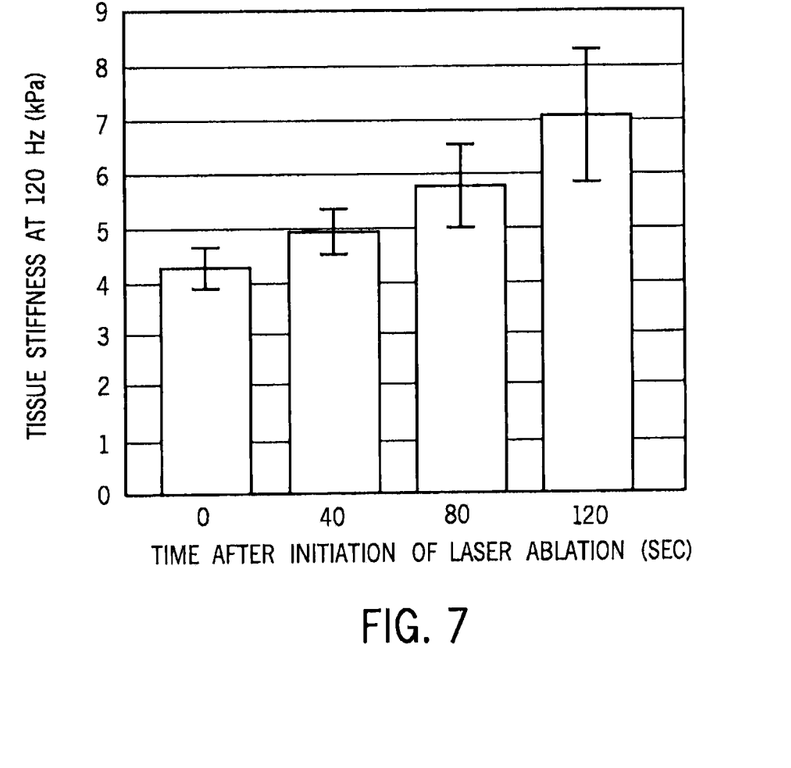
FIG. 7 is a graph showing stiffness measured at the tip of the laser applicator using the present invention demonstrating a measured increasing stiffness over the course of an ablation procedure.

The phantom studies demonstrate that the new sonoacoustic driver can produce mechanical waves along the shaft of the laser applicator with the mechanical waves radiating away from the shaft of the laser applicator. In vivo studies in porcine liver demonstrate that these waves can be produced and measured within the porcine liver in the coronal planes orthogonal to the laser applicator. The stiffness at the tip of the laser applicator can be measured at 40 second intervals during the ablation and demonstrates increasing stiffness over the course of the ablation, as illustrated in FIG. 7.

This and other similar porcine studies demonstrate the feasibility of using the path-thru driver to deliver mechanical waves through a medical device such as a polycarbonate laser fiber applicator into the organ tissue that is being ablated and to be able to measure differing tissue stiffness values in the ablation zone during the ablation. This becomes clinically attractive for at least two important reasons: the elastography images can be acquired during a breathhold with less susceptibility to motion artifact than temperature mapping phase imaging and the stiffness changes are permanent versus the transient changes seen with the temperature.

Figure 8:
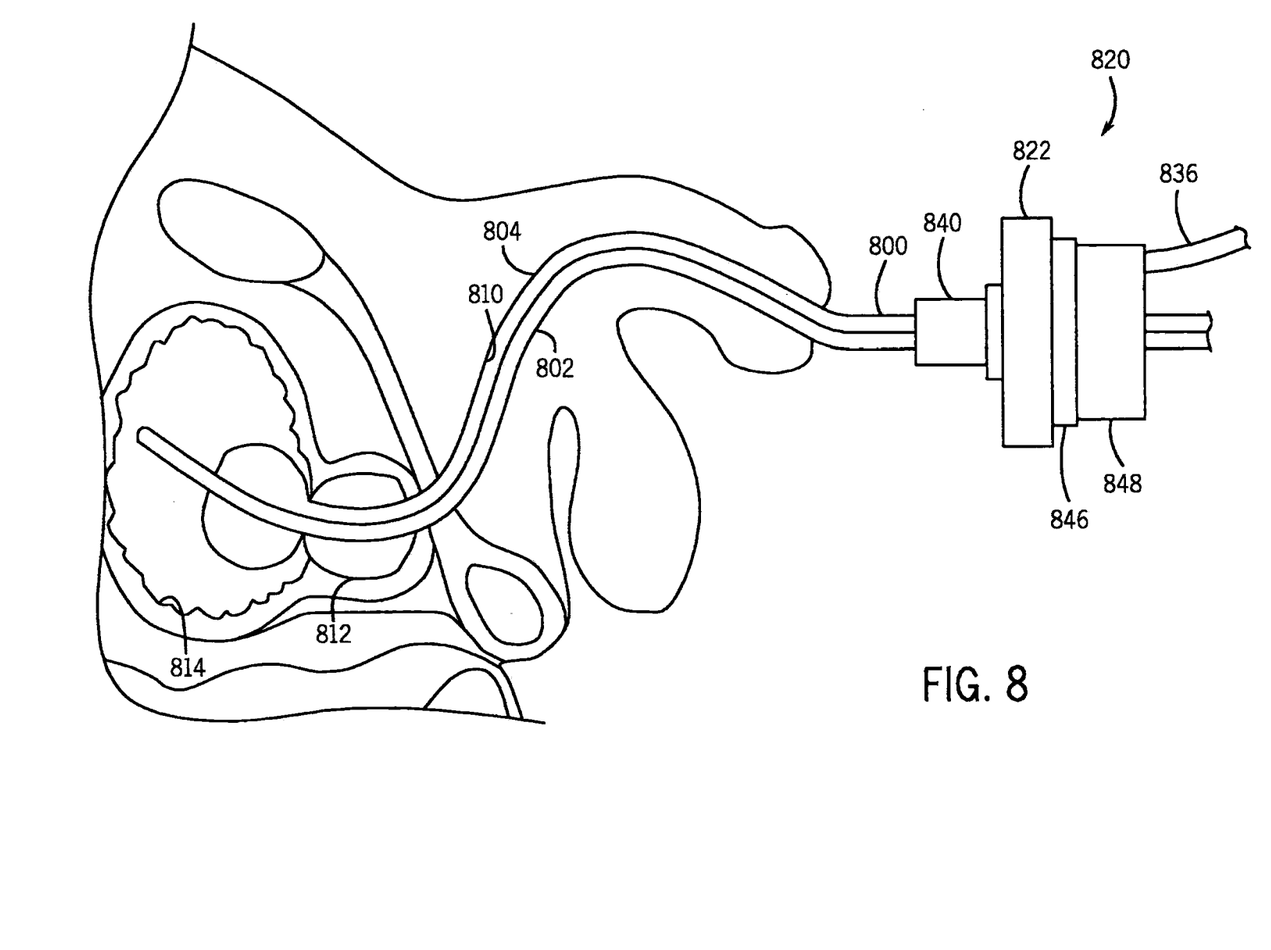
FIG. 8 is a side view of another configuration of the MRE driver and medical device in accordance with the present invention.
Figure 9:
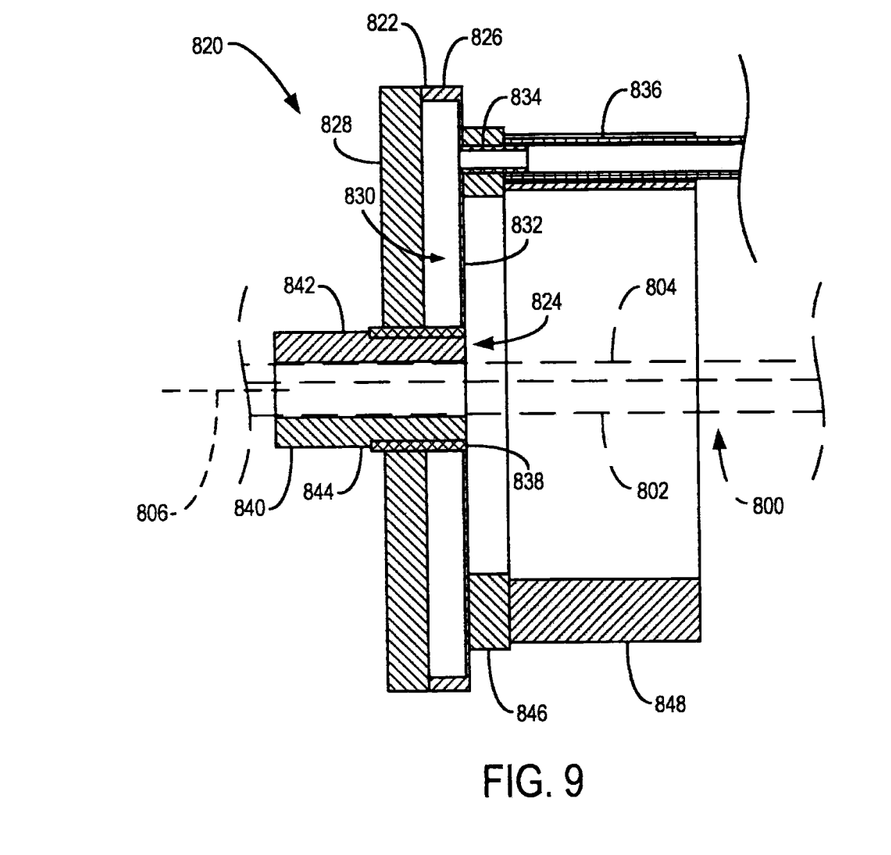
FIG. 9 is a side-sectional view of the configuration of the MRE driver of FIG. 8.

Referring now to FIGS. 8 and 9, another configuration of the inertial MRE driver 820 and an associated medical device 800 are illustrated in detail. In this configuration, the medical device 800 may be an MRI-compatible Foley or urologic catheter including a drainage lumen 802 and a balloon lumen 804. The catheter 800 is inserted into the subject's urethra 810, extends past the prostate 812, and enters the bladder 814 to facilitate, together with the MRE driver 820, transurethral prostate MRE in which shear waves are applied directly to the prostate 812.

Referring particularly to FIG. 9, the catheter 800 extends through the MRE driver 820 along a longitudinal axis 806 of the catheter. Specifically, the MRE driver 820 includes a housing 822 having a passage 824 to allow the catheter 800 to extend therethrough. The housing 822 includes an enclosure wall 826 and, connected thereto, a cover 828. Together, the cover 828 and the enclosure wall 826 define an internal housing chamber 830 in which the inertial driver 832 is disposed. In this configuration, the inertial driver 832 is an integrally connected and flexible diaphragm disposed within the internal housing chamber 830, specifically at an end thereof.

The flexible diaphragm 832 is configured to be elastically deformed and reciprocally actuated by a driving power (for example, pneumatic power) received via a port 834 extending through the diaphragm 832 and in fluid communication with the internal housing chamber 830. The port 834 is also in fluid communication with an inlet tube 836 to receive the driving power from a remotely located driver power assembly, such as the remotely located driver power assembly 306 of FIG. 3.

The diaphragm 832 connects to and, when actuated, displaces the catheter 800 via a seal ring 838 and a detachable holder 840 received in the passage 824. The seal ring 838 slidably engages the cover 828 within the passage 824. The seal ring 838 also surrounds and engages the detachable holder 840. The detachable holder 840 has two separable halves 842, 844 that together engage the catheter 800. The separable halves 842, 844 compress the catheter 800 to facilitate a firm connection, although not to an extent that prevents fluid drainage via the catheter 800.

Opposite the seal ring 838 and the detachable holder 840, the diaphragm supports a mounting annulus 846 and an annular weight 848. The annular weight 848 comprises a relatively dense material, such as lead or the like, to increase the peak actuating displacement of the diaphragm 832 and the catheter 800.

Testing of this configuration of the inertial MRE driver 820 and a 20 Fr. silicone Foley catheter was performed on a phantom forming an approximately 90 degree arcuate path. An FGREMRE sequence was developed and performed using a FOV=16 cm. In addition, NEX=4, Bandwidth=238 kHz, and TE/TR=50/21 msec were used. The results demonstrate that the catheter can be longitudinally displaced along its length when driven by the inertial MRE driver 820 and following a curved path.

In this configuration, the catheter is considered to perform a medical procedure by draining the subject's bladder. Even in instances in which the catheter does not drain the subject's bladder, placement of the catheter within the subject's urethra and bladder is also considered a medical procedure.

The present invention produces and delivers stress levels that are much larger than those produced by prior art drivers, even other passive acoustic drivers. The embodiments of the present invention closely and comfortably couple to the subject for consistent driver efficiency and imaging.

The invention claimed is:

1. A driver system for performing a magnetic resonance elastography (MRE) procedure using an MRI system to monitor operation of a medical device performing a medical procedure, the driver system comprising:
   a housing;
   a port located in the housing and configured to be connected to a driving power;
   an inertial driver arranged within the housing and configured to be moved within the housing by the driving power;
   a passage formed in the housing and extending along a longitudinal axis from a first opening in the housing, through the inertial driver, and to a second opening in the housing; and
   wherein the inertial driver is configured to receive a medical device extending through the passage and along the longitudinal axis and engage a portion of the medical device to impart oscillatory motion to the medical device as the inertial driver is moved within the housing by the driving power, wherein the oscillatory motion imparted by the inertial driver is configured to travel along the medical device as a waveguide to deliver the oscillatory motion to tissue receiving the medical procedure from the medical device to perform the MRE procedure.

2. The driver system of claim 1 wherein the inertial driver includes a piston configured to reciprocate within the housing.

3. The driver system of claim 2 wherein the piston is configured to fixedly engage the portion of the medical device to impart oscillatory motion to the medical device as the piston reciprocates within the housing.

4. The driver system of claim 2 wherein the piston is configured to removeably engage the medical device.

5. The driver system of claim 1 wherein the driving power includes pneumatic power.

6. The driver system of claim 1 wherein the medical device includes at least one of a laser ablation device, an endourethral catheter, an endorectal catheter, a Foley catheter, and a urologic catheter.

7. The driver system of claim 1 wherein the inertial driver is biased away from a first position.

8. The driver system of claim 1 wherein the medical device includes a catheter circulating a fluid to one of cool and heat the catheter, and the inertial driver is configured to connect to the catheter in a fluid-tight manner to inhibit the fluid from leaking from the catheter.

9. A driver system for performing a magnetic resonance elastography (MRE) procedure using an MRI system together with a medical device performing an interventional medical procedure, the driver system receiving a driving power from a driving power source, the driver system comprising:
   a housing defining a passage configured to receive a medical device extending there through, and the housing defining an internal chamber;
   a port connected to the housing and configured to receive the driving power from the driving power source, and the port being in fluid communication with the internal chamber to deliver the driving power to the internal chamber;
   an inertial driver arranged within the internal chamber and configured to connect to the medical device and to be moved by the driving power;
   wherein the inertial driver is configured to impart oscillatory motion to the medical device as the inertial driver is moved by the driving power, wherein the oscillatory motion imparted by the inertial driver is configured to travel along the medical device as a waveguide to deliver the oscillatory motion to tissue engaged with the medical device to perform the MRE procedure.

10. The driver system of claim 9 wherein the driving power includes pneumatic power.

11. The driver system of claim 10 wherein the inertial driver includes a piston configured to reciprocate within the internal chamber.

12. The driver system of claim 11 wherein the piston is configured to fixedly engage the medical device to impart oscillatory motion to the medical device as the piston reciprocates within the internal chamber.

13. The driver system of claim 10 wherein the inertial driver includes a flexible diaphragm disposed at an end of the internal chamber and configured to reciprocate relative to the housing.

14. The driver system of claim 9 wherein the inertial driver includes a holder configured to detachably engage and surround the medical instrument.

15. The driver system of claim 9 wherein the medical device includes at least one of a laser ablation device, an endourethral catheter, an endorectal catheter, a Foley catheter, and a urologic catheter.

16. The driver system of claim 9 wherein the inertial driver is biased away from a first position.

17. A driver system for performing a magnetic resonance elastography (MRE) procedure using an MRI system together with a medical device performing a interventional medical procedure, the driver system receiving a driving power from a driving power source, the driver system comprising:
   a housing having an enclosure wall;
   a port located in the housing and configured to receive the driving power;
   an inertial driver supported by the enclosure wall and configured to be moved relative to the enclosure wall by the driving power;
   a passage formed in the housing and extending along a longitudinal axis through the housing and the inertial driver; and
   wherein the inertial driver is configured to receive the medical device in the passage and along the longitudinal axis and engage a portion of the medical device to impart oscillatory motion to the medical device as the inertial driver is moved relative to the enclosure wall by the driving power, wherein the oscillatory motion imparted by the inertial driver is configured to travel along the medical device as a waveguide to deliver the oscillatory motion to tissue engaged with the medical device to perform the MRE procedure.

18. The driver system of claim 17 wherein the inertial driver includes a piston configured to reciprocate within an internal chamber defined by the enclosure wall.

19. The driver system of claim 17 wherein the inertial driver includes a flexible diaphragm disposed at an end of the enclosure wall and configured to reciprocate relative to the housing.

* * * * *